United States Patent
Yoo et al.

(10) Patent No.: US 9,522,383 B2
(45) Date of Patent: Dec. 20, 2016

(54) METHOD FOR PREPARING MAGNESIA-ZIRCONIA COMPOSITE CARRIER FOR CATALYZING OXIDATIVE DEHYDRATION OF NORMAL-BUTANE, METHOD FOR PREPARING MAGNESIUM ORTHOVANADATE CATALYST SUPPORTED BY MAGNESIA-ZIRCONIA COMPOSITE CARRIER PREPARED THEREBY, AND METHOD FOR PREPARING NORMAL-BUTENE AND 1,3-BUTADIENE USING MAGNESIUM ORTHOVANADATE CATALYST

(71) Applicant: SAMSUNG TOTAL PETROCHEMICALS CO., LTD., Seosan-si (KR)

(72) Inventors: Yeon Shick Yoo, Seosan-si (KR); Young Jin Cho, Seosan-si (KR); Jin Suk Lee, Seoul (KR); Ho Sik Chang, Daejeon (KR); In Kyu Song, Seoul (KR); Jong Kwon Lee, Daejeon (KR); Ho Won Lee, Seoul (KR)

(73) Assignee: HANWHA TOTAL PETROCHEMICAL CO., LTD., Seosan-Si (KR)

( * ) Notice: Subject to any disclaimer, the term of this patent is extended or adjusted under 35 U.S.C. 154(b) by 0 days.

(21) Appl. No.: 14/373,251

(22) PCT Filed: Oct. 15, 2012

(86) PCT No.: PCT/KR2012/008371
§ 371 (c)(1),
(2) Date: Jul. 18, 2014

(87) PCT Pub. No.: WO2013/108979
PCT Pub. Date: Jul. 25, 2013

(65) Prior Publication Data
US 2015/0024929 A1  Jan. 22, 2015

(30) Foreign Application Priority Data

Jan. 20, 2012 (KR) .......................... 10-2012-0006693

(51) Int. Cl.
*B01J 23/22* (2006.01)
*C07C 5/48* (2006.01)
(Continued)

(52) U.S. Cl.
CPC ................. *B01J 23/22* (2013.01); *B01J 23/02* (2013.01); *B01J 37/031* (2013.01); *C07C 5/48* (2013.01);
(Continued)

(58) Field of Classification Search
CPC ........... B01J 23/22; B01J 23/02; B01J 37/031; C07C 5/48; C07C 2523/22; C07C 2521/10; C07C 2521/06; Y02P 20/52
See application file for complete search history.

(56) References Cited

U.S. PATENT DOCUMENTS 3,303,234 A  2/1967 Bajars
3,914,332 A  10/1975 Dickason
(Continued)

FOREIGN PATENT DOCUMENTS

| JP | 2010-260793 | 11/2010 |
| KR | 10-1238553 | 2/2013 |
| KR | 10-1248697 | 3/2013 |

OTHER PUBLICATIONS

Lee et al., "Oxidative dehydrogenation of n-butane to n-butene and 1,3-butadiene over Mg3(VO4)2/MgO—ZrO2 catalysts: Effect of Mg:Zr ratio of support," Journal of Industrial and Engineering Chemistry 18 (2012) 1096-1101. Published Online Dec. 30, 2011.*
(Continued)

*Primary Examiner* — Anthony J Zimmer
(74) *Attorney, Agent, or Firm* — Harness, Dickey & Pierce, P.L.C.

(57) ABSTRACT

The present invention discloses a method of producing a magnesia-zirconia complex carrier for a catalyst for oxidative dehydrogenation of n-butane by sol-gel method; a method of producing a magnesium orthovanadate catalyst containing vanadium supported by said magnesia-zirconia complex carrier; and a method of producing n-butene and 1,3-butadiene using said catalyst.

7 Claims, 4 Drawing Sheets

(51) Int. Cl.
*B01J 37/03* (2006.01)
*B01J 23/02* (2006.01)

(52) U.S. Cl.
CPC ....... *C07C 2521/06* (2013.01); *C07C 2521/10* (2013.01); *C07C 2523/22* (2013.01); *Y02P 20/52* (2015.11)

(56) References Cited

U.S. PATENT DOCUMENTS

| | | | |
|---|---|---|---|
| 4,777,319 A * | 10/1988 | Kung | C07C 5/48 585/443 |
| 6,187,984 B1 | 2/2001 | Wu et al. | |
| 6,433,241 B2 | 8/2002 | Wu et al. | |
| 6,586,360 B1 | 7/2003 | Ingallina et al. | |
| 8,927,455 B2 | 1/2015 | Cho et al. | |
| 2012/0232320 A1 * | 9/2012 | Song | C07C 5/48 585/627 |

OTHER PUBLICATIONS

Lee et al., "Oxidative dehydrogenation of n-butane over Mg3(VO4)2/MgO—ZrO2 catalysts: Effect of oxygen capacity and acidity of the catalyst," Journal of Industrial and Engineering Chemistry 18 (2012) 1758-1763. Published Online Apr. 5, 2012.*
Murgia et al., Sol-gel synthesis of V2O5—SiO2 catalyst in the oxidative dehydrogenation of n-butane, 2006, pp. 134-143.
Armendariz et al., Oxidative dehydrogenation of n-butane on zinc-chromium ferrite catalysts, 1994, pp. 325-332.
Kung, Desirable Catalyst Properties in Selective Oxidation Reactions, 1986, pp. 171-178.
Nieto et al., Oxidative dehydrogenation of n-butane on MgO-supported vanadium oxide catalysts, 1998, pp. 215-228.
Bhattacharyya et al., Oxidative dehydrogenation of n-butane to butadiene, 1992, pp. 29-43.
Marcu et al., Oxidehydrogenation of n-butane over tetravalent metal phosphates based catalysts, 2002, pp. 309-320.
Madeira et al., Electrical conductivity, basicity and catalytic activity of Cs-promoted a-NiMoO4 catalysts for the oxidative dehydrogenation of n-butane, 1997, pp. 243-256.
Lemonidou et al., Investigations on the oxidative dehydrogenation of n-butane over VMgO-type catalysts, 1998, pp. 65-71.
Chaar et al., Selective Oxidative Dehydrogenation of Butane over V—Mg—O Catalysts, 1987, pp. 483-498.
Chaar et al., Selective Oxidative Dehydrogenation of Propane over V—Mg—O Catalysts, 1988, pp. 463-467.
Owen et al., Effect of cation reducibility on oxidative dehydrogenation of butane on orthovanadates, 1993, pp. 265-284.
Harlin et al. Alumina-Supported Vanadium Oxide in the Dehydrogenation of Butanes, 2000, pp. 67-78.
Jiang et al., Preparation of ZrO2-supported MgO with high surface area and its use in mercaptan oxidation of jet fuel, 2000, pp. 169-176.
Gazzoli et al., Bulk and surface structures of V2O5/ZrO2 catalysts for n-butane oxidative dehydrogenation, 2009, pp. 17-23.
Kijima et al., A Chemical Potential Diagram and an In-situ X-ray Diffraction Analysis of a V—Mg—O Catalyst Used in the Oxidative Dehydrogenation of n-Butane, 2009, pp. 63-69.
Murgia et al., Sol—gel synthesis of V2O5-SiO2 catalyst in the oxidative dehydrogenation of n-butane, 2006, pp. 134-143.
Urlan et al., Oxidative dehydrogenation of n-butane over titanium pyrophosphate catalysts in the presence of carbon dioxide, 2008, pp. 2403-2406.

* cited by examiner

METHOD FOR PREPARING MAGNESIA-ZIRCONIA COMPOSITE CARRIER FOR CATALYZING OXIDATIVE DEHYDRATION OF NORMAL-BUTANE, METHOD FOR PREPARING MAGNESIUM ORTHOVANADATE CATALYST SUPPORTED BY MAGNESIA-ZIRCONIA COMPOSITE CARRIER PREPARED THEREBY, AND METHOD FOR PREPARING NORMAL-BUTENE AND 1,3-BUTADIENE USING MAGNESIUM ORTHOVANADATE CATALYST

TECHNICAL FIELD

The present invention relates to a method of producing magnesia-zirconia complex carrier for a catalyst for oxidative dehydrogenation of normal-butane (hereinafter, referred as n-butane), a method of producing a magnesia-zirconia complex carrier-supported magnesium orthovanadate catalyst by supporting vanadium to the magnesia-zirconia complex carrier, and a method of producing n-butene and 1,3-butadiene using said catalyst.

BACKGROUND OF THE INVENTION

Recently, a demand for polymer products has rapidly increased worldwide, particularly, in China. Therefore, production and stable supply of light olefins as raw materials for producing these products has become very important. Among those light olefins, demand for and value of n-butene and 1,3-butadiene which serve as a raw material for various synthetic rubber and copolymer products are increasing currently, and methods for producing them include three methods such as naphtha cracking, direct dehydrogenation of n-butane or n-butene, and oxidative dehydrogenation of n-butane or n-butene.

In recent years, as for a naphtha cracking process which contributes more than about 90% of normal-butene and 1,3-butadiene supply, new establishment or expansion plans have been reported one after another, and actually, the factories have been in operation. However, although such new establishment or expansion plans of naphtha cracking center seem to be sufficient for a recently increasing demand for normal-butene and 1,3-butadiene as raw materials for producing synthetic rubber and polyethylene products, a look at naphtha crackers being established exhibits that they are not. For example, a gas cracker being established in the Middle East and using a low-priced gas as a raw material is intended to produce olefins such as ethylene, propylene, etc, and thus has a low yield with respect to $C_4$ mixtures. Therefore, new establishment or expansion of naphtha cracking center only for the purpose of increasing the production of n-butene and 1,3-butadiene is hardly considered, and if so, it would cause further problems of surplus production of other basic petrochemical feedstocks other than n-butene and 1,3-butadiene. Moreover, with an increasing demand for ethylene and propylene in the recent petrochemical market, new establishment and operation regarding a naphtha cracking process tends to be rather focused to increase in production yield of ethylene and propylene. In addition to that, with the continuous price increase in naphtha raw materials for C4 production, a naphtha cracking process is modified as a process using light hydrocarbons such as ethane, propane, etc. as a raw material which can result in high production yield for basic petrochemical feedstock such as ethylene, propylene and the like, although its yield for C4 mixtures is low, and thus the proportion of a process for obtaining C4 mixture in the naphtha cracking process is relatively reduced. Therefore, it is getting more difficult to obtain $C_4$ mixtures, particularly normal-butene and 1,3-butadiene, by the naphtha cracking process.

As the foregoing description, although n-butene and 1,3-butadiene supply majorly depend on a naphtha cracking process, based on the many reasons as above, the naphtha cracking process cannot be an alternative way to resolve the imbalance between supply and demand, caused by recent increased demand in n-butene and 1,3-butadiene. In this circumstance, a dehydrogenation reaction in which hydrogens are removed from n-butane thus obtaining n-butene and n-butene, is attracting great attention as an effective process for responding to the increased demand for n-butene and 1,3-butadiene, and thus many studies regarding that are being made [Non-Patent Documents 1 to 4].

The dehydrogenation reaction of n-butane can be classified into direct dehydrogenation and oxidate dehydrogenation, wherein the direct dehydrogenation reaction of n-butane is highly exothermic and thus a thermodynamically disadvantageous reaction since hydrogen should be directly detached from a chemically stable n-butane as well as requires great energy consumption to satisfy the high-temperature reaction condition. For carrying out direct dehydrogenation, used are precious metal catalysts such as platinum or palladium. However, such precious metal catalysts have a problem of requiring a reactivation process owing to their short lifetime in most cases, therefore the direct dehydrogenation is not a suitable commercial process for producing 1,3-butadiene [Patent Documents 1 to 2].

On the contrary, unlike the direct dehydrogenation, the oxidative dehydrogenation of n-butane is the reaction wherein n-butane and oxygen reacts to produce n-butene and water, or 1,3-butadiene and water, and thus, compared to the direct dehydrogenation, it is thermodynamically advantageous due to the generation of stable water, and since an endothermic reaction turns to an exothermic reaction with the generation of water, and rapid temperature changes in catalyst layer which can caused by the heat from the catalyst reaction can be prevented by water generated after the reaction. By such reasons, the oxidative dehydrogenation process of n-butane can be operated under process conditions more advantageous than those of the direct dehydrogenation process. Therefore, when a catalyst process for producing n-butene and 1,3-butadiene with high efficiency is developed, this process can be used as an effective alternative to prior processes to produce n-butene and 1,3-butadiene through an independent energy-saving process.

As described above, although the oxidative dehydrogenation of n-butane has many advantages over the direct dehydrogenation of n-butane in many ways such as a thermodynamic aspect which makes possible to produce n-butene and 1,3-butadiene with a high yield, under mild reaction conditions, it has a drawback that many side reactions such as highly oxidative reactions which involve generation of carbon monoxide or carbon dioxide owing to the use of oxygen as a reactant. Therefore, in order to commercialize the oxidative dehydrogenation of n-butane, the most crucial technical point is to achieve a catalyst with highly increased selectivity to n-butene and 1,3-butadiene by preventing side reactions such as complete-oxidative reactions, while achieving the conversion of n-butane to the maximum.

Although the reaction mechanism of the oxidative dehydrogenation of n-butane has not yet been exactly known, it is reported that, as a first step, hydrogen is detached from n-butane adsorbed to a solid catalyst due to a reaction between metallic active sites and lattice oxygen of the catalyst at the same time when a redox reaction of the catalyst occurs with a loss of the lattice oxygen from the catalyst, and therefore complex oxide catalysts containing transition metal ions which may be in various oxidation states are essential to this oxidative dehydrogenation reaction [Non-Patent Document 5].

So far, cataslyts known to effectively produce n-butene and 1,3-butadiene through oxidative dehydrogenation of n-butane are magnesium orthovanadate catalysts [Non-Patent Documents 4 and 6 to 8, and Patent Documents 3 to 5]; vanadium oxide catalysts [Non-Patent Documents 9 to 10, and Patent Document 6]; pyrophosphate catalysts [Non-Patent Documents 2 and 11]; ferrite catalysts [Non-Patent Document 12 and Patent Document 7] and the like. The characteristic feature shared by the above complex oxide catalysts is the presence of transition metals, which are necessary for transition of electrons between the catalyst and n-butane via the redox reaction of the catalyst as explained above [Non-Patent Document 13]. The catalysts can carry out the oxidative dehydrogenation of n-butane by incorporating metals which can be oxidized and reduced such as, for example, vanadium, iron, nickel and titanium, etc, and among them, particularly, magnesium orthovanadate catalysts which contain vanadium are known to have high activity, based on which it is considered for the redox potential of vanadium metal to be suitable for the oxidative dehydrogenation of n-butane [Non-Patent Documents 6 to 7].

Magnesium orthovanadate catalysts are generally produced to be the form in which the active phase of $Mg_3(VO_4)_2$ is supported by a separate metal oxide. It is reported that when magnesium orthovanadate catalysts are not supported, the activity is lower than that of supported magnesium orthovanadate. For example, some results of oxidative dehydrogenation of n-butane by using unsupported magnesium orthovanadate catalysts have been reported in conventional patents and literatures, specifically, for example, 11.5% of n-butane conversion rate, 6.7% of dehydrogenation product yield under the conditions of 540° C. and the feed composition ratio of n-butane:oxygen:helium=4:8:88 [Non-Patent Document 8], and 5.7% dehydrogenation product yield under the conditions of 540° C. and the feed composition ratio of n-butane:oxygen:helium=5:10:85 [Non-Patent Document 4]. Further, it was reported that an oxidative dehydrogenation reaction of n-butane under the conditions of 540° C. and the feed composition ratio of n-butane:oxygen=1:2 using an unsupported magnesium orthovanadate catalyst resulted in a n-butane conversion rate of 10.5% and a dehydrogenation product yield of 5.7% [Non-Patent Document 4].

When magnesium orthovanadate catalysts are supported, the activity can be more improved. Specifically, magnesia supported magnesium orthovanadate catalysts obtained by supporting vanadium to excessive amount of magnesia and their excellent activity for the oxidative dehydrogenation of n-butane have been generally reported. Specifically, it was reported that when the oxidative dehydrogenation of n-butane under the conditions of 600° C. and the composition ratio of n-butane:oxygen:nitrogen of 2:1:97 was conducted by using a magnesia-supported magnesium orthovanadate catalyst obtained by mixing magnesium hydroxide with a mixed aqueous solution of ammonium vanadate and ammonia with the ratio of Mg to V of 6:1, it resulted in 30.4% of n-butane conversion rate, 70.6% of dehydrogenation product selectivity and 21.5% of dehydrogenation product yield [Non-Patent Document 1], and when the oxidative dehydrogenation of n-butane under the conditions of 540° C. and the composition ratio of n-butane:oxygen:helium of 5:10:85 was conducted by using a magnesia-supported magnesium orthovanadate catalyst, it resulted in the yield of 22.8% [Non-Patent Document 4]. Further, also reported were the results of 35.4% of n-butane conversion rate and 18.1% of dehydrogenation product yield by the oxidative dehydrogenation of n-butane under the conditions of 550° C. using a magnesia-supported magnesium orthovanadate catalyst under the higher oxygen conditions wherein the feed composition ratio of n-butane:oxygen:helium=5:20:75 [Non-Patent Document 14].

Further reported was a method for using magnesium orthovanadate catalyst which makes possible to increase the activity for the oxidative dehydrogenation of n-butane by mixing additives to magnesia-supported magnesium orthovanadate catalyst so as to obtain products from the dehydrogenation, n-butene and 1,3-butadiene with high yield in the literature of [Non-Patent Document 15], wherein the dehydrogenation was carried out under the conditions of 570° C., a composition ratio of n-butane:oxygen:nitrogen of 4:8:88 by using 25 wt % of a magnesia-supported magnesium orthovanadate catalyst further mixed with titanium oxide and chromium oxide, resulting in 54.0% of n-butane conversion rate and 33.8% of dehydrogenation product yield.

The magnesia-supported magnesium orthovanadate catalyst makes it possible to obtain n-butene and 1,3-butadiene at a very high yield in an oxidative dehydrogenation reaction of n-butane, but oxidation-reduction of the catalyst which should be reversibly carried out in a catalytic reaction is non-reversibly carried out [Non-Patent Document 1], and, thus, the high activity of the magnesia-supported magnesium orthovanadate catalyst is not maintained for a long time. Therefore, it is limited in application as a commercialized process.

With a purpose to overcome the limits of magnesia-supported magnesium orthovanadate catalysts of the prior arts, the present inventors have developed and reported a method of producing a magnesia-zirconia complex carrier-supported magnesium orthovanadate catalyst which is thermally and chemically stale and does not have any problem regarding a decrease in catalytic activity over time in magnesia-supported magnesium orthovanadate catalysts or a low activity in vanadium-based catalysts of the prior arts; and a method for producing n-butene and 1,3-butadiene with a stable and high yield, using the catalyst produced by the above method [Patent Documents 3 to 5]. Specifically, in the previous patents, the present inventors produced a magnesia-zirconia complex carrier for a catalyst for an oxidative dehydrogenation of n-butane by gel-oxalate method, and produced a magnesia-zirconia complex carrier-supported magnesium orthovanadate catalyst by supporting vanadium to the carrier; and thereby established a catalytic process for producing n-butene and 1,3-butadiene with a stable and high yield, using the catalyst.

SUMMARY OF THE INVENTION

Thus, the present inventors reported a production method of a magnesia-zirconia complex carrier-supported magnesium orthovanadate catalyst which does not exhibit any deactivation of the catalyst when it is applied to an oxidative dehydrogenation reaction of n-butane and has high yields of normal-butene and 1,3-butadiene, as disclosed in the previously published patent documents [Patent Documents 3 to 5]

of the present inventors. Further, the present inventors conceived a production method of a magnesia-zirconia complex carrier by means of a sol-gel method using a citric acid through additional and continuous studies and established a production method of a magnesia-zirconia complex carrier-supported magnesium orthovanadate catalyst by supporting vanadium to the carrier, thereby obtaining reproducibility in producing a catalyst with high efficiency. Further, the present inventors have developed a catalytic reaction process by which n-butene and 1,3-butadiene can be produced with high yields using the catalyst produced as such, and completed the present invention based thereon.

Therefore, an object of the present invention is to provide a production method of a magnesia-zirconia complex carrier prepared by a sol-gel method using a citric acid in order to produce a carrier which is configured to support an active component formed of magnesium orthovanadate and does not decrease an activity of magnesium orthovanadate but obtains a high activity even when it is applied to an oxidative dehydrogenation reaction of n-butane, by a more simple process with reproducibility in producing a catalyst.

Another object of the present invention is to provide a method for producing a magnesia-zirconia complex carrier-supported magnesium orthovanadate catalyst for an oxidative dehydrogenation reaction of n-butane, comprising supporting the active component, magnesium orthovanadate to the magnesia-zirconia complex carrier obtained by the method according to the present invention.

Yet another object of the present invention is to provide a method for producing n-butene and 1,3-butadiene from n-butane, comprising performing an oxidative dehydrogenation reaction of n-butane which can obtain a stable and high activity, using the catalyst in which magnesium orthovanadate is supported by the magnesia-zirconia complex carrier prepared by the above-described production method.

DETAILED DESCRIPTION OF THE INVENTION

The present invention provides a method for preparing a magnesia-zirconia complex carrier for a catalyst for oxidative dehydrogenation of n-butane comprising the following steps:
(a) preparing a mixed precursor solution of magnesium and zirconium by dissolving a magnesium precursor and a zirconium precursor in a first solvent;
(b) preparing a solid acid solution by dissolving a solid acid in a second solvent;
(c) preparing a carrier forming solution by mixing the mixed precursor solution prepared in the step (a) and the solid acid solution prepared in the step (b); and
(d) producing a magnesia-zirconia complex carrier for a catalyst of an oxidative dehydrogenation of n-butane by heat-drying the carrier forming solution prepared in the step (c) and heating a resultant solid product.

As for the magnesium precursor and the zirconium precursor used in the above step (a), any conventionally used precursors may be used without limitation. Generally, the magnesium precursor may preferably include at least one selected from a chloride or a nitrate of magnesium, and the zirconium precursor may preferably include at least one selected from a chloride, an oxynitrate, or oxychloride of zirconium. Particularly, magnesium nitrate and zirconium oxynitrate may be preferably used.

A ratio of the magnesium precursor and the zirconium precursor used in the step (a) is not specifically limited, but in order to produce a carrier for a magnesium orthovanadate catalyst of which a high activity can be stably maintained for a long time, a molar ratio of zirconium:magnesium is preferably 0.5 to 16:1 and more preferably about 1 to 16:1.

The first solvent and the second solvent used in the steps (a) and (b) respectively may be selected from water and alcohol and may be preferably water, but may not be limited thereto.

The solid acid used in the step (b) may include at least one selected from the group consisting of a citric acid, a succinic acid, a malic acid, and a tartaric acid, but may not be limited thereto.

Regarding an amount of the solid acid dissolved in the second solvent in the step (b) and a mixing ratio of the mixed precursor solution and the solid acid solution in the step (c), a molar ratio of the solid acid dissolved in the second solvent and a combination of the magnesium precursor and the zirconium precursor is preferably 0.5 to 2:1, and more preferably 1:1 in order to convert all of magnesium ions and zirconium ions to magnesium solid acid salt and zirconium solid acid salt. If they are added at a molar ratio of less than 0.5:1, a dispersion may be decreased. On the other hand, if they are added at a molar ratio of more than 2:1, undesirably, a viscosity may be increased.

The heat-drying in the step (d) may be carried out at a temperature in the range of 40 to 200° C., and may be carried out through the following two steps. In the first step, the carrier forming solution is heat-dried at a temperature in the range of 40 to 80° C. until a complex metal oxide precursor in the form of a solid sponge is formed. In the second step, the complex metal oxide precursor is heat-dried at a temperature in the range of 100 to 200° C. for 2 hours or more. Through the heat-drying, the first solvent, the second solvent, and a by-product gas such as $NO_x$ can be removed. If the heat-drying is carried out at a temperature in the above range (40 to 200° C.), the first solvent, the second solvent, and the by-product gas such as $NO_x$ can be completely removed.

Further, the heating process may be carried out at a temperature in the range of 400 to 1000° C. for 1 to 12 hours, and preferably at a temperature in the range of 500 to 700° C. for 3 to 6 hours, thereby obtaining a magnesia-zirconia complex carrier. The dried solid sample is heated in order to not only synthesize magnesia-zirconia from the magnesium solid acid salt and the zirconium solid acid salt but also suppress denaturation of a carrier-supported catalyst when the catalyst is used in an oxidative dehydrogenation reaction of n-butane considering a reaction temperature of the reaction. If the heating is carried out at a temperature of less than 400° C. or for a time of less than 1 hour, undesirably, the magnesium solid acid salt and the zirconium solid acid salt are not sufficiently conversed to the magnesia-zirconia, and if the heating is carried out at a temperature of more than 1000° C. or for a time of more than 12 hours, a crystal phase of zirconia in the magnesia-zirconia complex carrier is changed, and thus, undesirably, it may not be appropriately used as a carrier.

The method for preparing a magnesium orthovanadate catalyst supported by the magnesia-zirconia complex carrier using the magnesia-zirconia complex carrier prepared as the above described method comprises the following steps:
(i) impregnating the magnesia-zirconia complex carrier prepared by the above described method with an aqueous vanadate solution;
(ii) preparing a magnesia-zirconia complex carrier-supported magnesium orthovanadate catalyst by drying and heating the product obtained from the above step (i).

As for the vanadate used in the method for preparing a catalyst of the present invention, any conventional vanadate may be used, for example, ammonium metavanadate may be preferably used without being limited to this, and other conventional vanadate may be further used depending on the purposes. When using ammonium metavanadate, the ammonium ions escape during the impregnation, drying and heating processes, and thus it is possible to minimize the effect of the ions, thereby being suitably used as a vanadate to be supported to magnesia-zirconia complex carrier.

The aqueous vanadate solution may be prepared by dissolving vanadate into an aqueous oxalic acid solution or an aqueous ammonia solution (ammonia water). In the aqueous solution of vanadate, the amount of water may be enough if it can dissolve the salt, and preferably water is used at the minimum as long as it can dissolve the salt sufficiently. When dissolving the vanadate, as for the oxalic acid or an aqueous ammonia solution for helping dissolution of the vanadate, any commercially available products on the market may be used without limitation, for example oxalic acid dihydrate may be preferably used.

The drying process in the step (ii) is to remove the moisture remained after the impregnation of vanadate, wherein the temperature and time for drying may be determined according to the general drying conditions in the art, for example the drying temperature may be 50-200° C., preferably 70-120° C., and the drying time may be 3-24 hours and preferably 6-12 hours.

Further, the heating process in the above step (ii) is carried out to remove oxalic acid which is used to dissolve and impregnate vanadate, and to synthesize magnesium orthovanadate supported from the vanadate supported by the magnesia-zirconia complex carrier. For example, it is carried out at the temperature in the range of 350-800° C. and preferably 500-700° C., for 1-12 hours and preferably 3-6 hours, wherein when the temperature is less than 350° C. or the time is less than 1 hour, the magnesia orthovanadate synthesis may not be sufficiently conducted, and when the temperature is more than 800° C. or the time is more than 12 hours, the crystalline structure of zirconia in the magnesia-zirconia complex carrier can be changed, disadvantageously.

The magnesium orthovanadate catalyst supported by the magnesia-zirconia complex carrier of the present invention as prepared by the above-described method, is developed through additional and continuous studies on a production method of a magnesia-zirconia complex carrier-supported magnesium orthovanadate catalyst by a conventional technology [Patent Document 5] for an oxidative dehydrogenation reaction of n-butane to produce n-butene and 1,3-butadiene. According to the present invention, magnesia-zirconia complex carrier is synthesized by a production method different from those of the previous patents, and a magnesia-zirconia complex carrier can be produced at an optimum mixing ratio of magnesia and zirconia by a sol-gel method using solid acid.

The sol-gel method of the present invention has an advantage of simple synthesis and an advantage of being able to obtain a magnesia-zirconia complex carrier having uniform properties for the obtained magnesia-zirconia constitution. Additionally, it does not have any problem in the processability of the magnesia-zirconia complex carrier, and it can be directly applied to oxidative dehydrogenation of n-butane without requiring a separate activation step under the reaction conditions, thereby being directly applied to commercial processes.

Further, the present invention is to provide a method for preparing n-butene and 1,3-butadiene which comprises carrying out oxidative dehydrogenation of n-butane on the magnesium orthovanadate catalyst supported by the zirconia carrier or magnesia-zirconia complex carrier prepared by the above-described method.

The reactant for the oxidative dehydrogenation of n-butane is a mixed gas comprising n-butane, oxygen and nitrogen, at the ratio by volume of n-butane:oxygen:nitrogen=2-10:0.5-40:50-97.5, preferably n-butane:oxygen:nitrogen=4:2-20:76-94, more preferably 4:2-10:86-94. When the volume ratio of n-butane, oxygen and nitrogen is out of said range, a side reaction, i.e. complete oxidation during the oxidative dehydrogenation of n-butane occurs greatly; the catalyst activity becomes lowered and process safety is not good, disadvantageously.

When feeding the reactant in the form of a mixed gas to a reactor, the amount of the reactant being fed which may be adjusted by a mass flow meter controller is adjusted to be preferably 50-5000 $h^{-1}$, preferably 500-3000 $h^{-1}$, more preferably 1000-2000 $h^{-1}$ of Gas hourly space velocity (GHSV) based on the amount of n-butane. When the space velocity is less than 50 $h^{-1}$, the catalyst reaction is localized to a limited section, leading to coking of the side products from the catalyst reaction, or heat emitted during the reaction may cause a hot spot, disadvantageously, and when the speed is more than 5000 $h^{-1}$, the catalyst reaction cannot sufficiently occur in the reactant passing the catalyst bed, disadvantageously.

The temperature for carrying out the oxidative dehydrogenation of n-butane is preferably maintained at the range of 300-800° C., more preferably 450-600° C., and most preferably 500° C. When the reaction temperature is less than 300° C., n-butane cannot be sufficiently activated, and when it is more than 800° C., decomposition reaction of n-butane occurs, disadvantageously.

INDUSTRIAL AVAILABILITY

According to the present invention, the magnesia-zirconia complex carrier can be easily produced by a simple synthesis process, and excellent reproducibility in producing a carrier can be obtained. Further, since a subsequent process of supporting vanadium is simply carried out, a production process of a magnesia-zirconia complex carrier-supported magnesium orthovanadate catalyst finally obtained also guarantees reproducibility. Therefore, it is possible to stably obtain a magnesia-zirconia complex carrier-based magnesium orthovanadate catalyst for an oxidative dehydrogenation reaction of n-butane that makes it possible to prepare n-butene and 1,3-butadiene with high yields.

Further, according to the present invention, n-butene and 1,3-butadiene for which demand and value are gradually increasing owing to their wide use as intermediates for various petrochemical products in petrochemical industry can be prepared from n-butane which does not have wide applications, thereby being possible to achieve highly added value of C4 petrochemical feedstocks. Additionally, by the present invention, it is possible to ensure a process dedicated to the production of n-butene and 1,3-butadiene without new establishment of additional naphtha crackers, thereby satisfying demand for n-butene and 1,3-butadiene and acquiring economic benefits while actively coping with the market changes in the future.

EXAMPLES

Hereinafter, the present invention is further illustrated in detail via specific examples as given below. However, it should be understood that the following examples are described only for an illustrative purpose, without any intention to limit the scope of the present invention.

Preparation Example 1

Production of Magnesia-Zirconia Complex Carrier (MgO—ZrO$_2$) by Sol-Gel Method

In order to prepare 2.5 g of a magnesia-zirconia complex carrier having a molar ratio of magnesia:zirconia=4:1 by a sol-gel method, 9.1 g of magnesium nitrate and 2.1 g of zirconium oxynitrate were dissolved into distilled water (12 ml) so as to prepare a mixed precursor solution of magnesium and zirconium at the same time when 8.5 g of a citric acid was dissolved into distilled water (9 ml) so as to prepare a citric acid solution. After the precursor solution and the citric acid solution were mixed to prepare a carrier forming solution, the carrier forming solution was heated at 70° C. with stirring. Then, when the carrier forming solution was swollen with generation of a NO$_x$ gas, a beaker in which the carrier forming solution was placed was transferred to an oven and then dried at 170° C. for about 12 hours so as to completely remove the NO$_x$ gas contained in the carrier forming solution. As a result, a carrier precursor in the form of a solid sponge was obtained. Then, the carrier precursor was ground to powder and heated in an electric furnace in air atmosphere at a constant temperature of 550° C. for hours, thereby producing a magnesia-zirconia complex carrier by the sol-gel method.

Comparative Preparation Example 1

Production of Magnesia-Zirconia Complex Carrier (MgO—ZrO$_2$) by Gel-Oxalate Method For comparison with the magnesia-zirconia complex carrier produced by the method according to Preparation Example 1, the inventors of the present invention produced magnesia-zirconia complex carrier (MgO—ZrO$_2$) through synthesis by a gel-oxalate method according to the previous patent by the present inventors [Patent Document 5], and the production method in detail was as follows.

In order to prepare 5 g of a magnesia-zirconia complex carrier having a molar ratio of magnesia:zirconia=4:1 by a gel-oxalate precipitation method, 6.7 g of magnesium chloride and 4.1 g of zirconium chloride were dissolved into ethanol (500 ml) so as to prepare a mixed ethanol solution of magnesium and zirconium at the same time when 26.6 g of oxalic acid dihydrate was dissolved into ethanol (130 ml) so as to prepare an ethanol solution of oxalic acid. After dissolution was sufficiently achieved in each solution, the ethanol solution of oxalic acid was injected to the mixed ethanol solution of magnesium and zirconium with a syringe pump as slowly as possible, and the mixture was sufficiently stirred. Thus obtained mixed solution was again stirred at room temperature for 3 hours with a magnetic stirrer for sufficient agitation, and allowed to stand still at room temperature for 12 hours for the subsequent phase separation. In order to remove unnecessary ions such as chloride from the phase-separated mixed solution, the ethanol solution was filtered and the filtered material was again washed with the ethanol solution and stirred, and this same procedure was conducted several times. Then, the final solution having precipitates was centrifuged and thus obtained solid sample was dried at 80° C. for 12 hours. Thus prepared solid sample was heated in an electric furnace in air atmosphere at a constant temperature of 550° C. for 3 hours, thereby producing a magnesia-zirconia complex carrier prepared by the single-step gel-oxalate method.

Preparation Example 2

Production of Magnesium Orthovanadate Catalyst Containing Vanadium of 5.6 Weight % Supported by Magnesia-Zirconia Complex Carrier by Supporting Vanadate 0.14 g of ammonium vanadate was dissolved and immersed in a small amount of oxalic acid aqueous solution in which 0.31 g of oxalic acid was dissolved such that an amount of vanadium supported was 5.6 weight % with respect to 1 g of each magnesia-zirconia carrier obtained by the method of Preparation Example 1 and Comparative Preparation Example 1, and thus obtained solution was dried at 80° C. for 12 hours and a solid sample was obtained. Thus prepared solid sample was heated in an electric furnace in air atmosphere at a constant temperature of 550° C. for hours, thereby producing a magnesium orthovanadate catalyst containing vanadium of 5.6 weight % supported by a magnesia-zirconia complex carrier.

Preparation Example 3

Production of Magnesium Orthovanadate Catalyst Including Vanadium of 11.2 Weight % Supported by Magnesia-Zirconia Complex Carrier by Supporting Vanadate 0.32 g of ammonium vanadate was dissolved and immersed in a small amount of oxalic acid aqueous solution in which 0.69 g of oxalic acid was dissolved such that an amount of vanadium supported was 11.2 weight % with respect to 1 g of each magnesia-zirconia carrier obtained by the method of Preparation Example 1 and Comparative Preparation Example 1, and thus obtained solution was dried at 80° C. for 12 hours and a solid sample was obtained. Thus prepared solid sample was heated in an electric furnace in air atmosphere at a constant temperature of 550° C. for hours, thereby producing a magnesium orthovanadate catalyst containing vanadium of 11.2 weight % supported by a magnesia-zirconia complex carrier.

Preparation Example 4

Production of Six Species of Magnesium Orthovanadate Catalysts with Various Contents of Vanadium Supported by Magnesia-Zirconia Complex Carrier (MgO—ZrO$_2$) Prepared by Sol-Gel Method Magnesia-zirconia complex carriers were prepared by the methods of Preparation Examples 1 and 2 of the present invention, and six species of magnesium orthovanadate catalysts with various contents of vanadium supported were prepared. To be specific, an amount of vanadium to be supported in the magnesia-zirconia complex carrier prepared by the sol-gel method was adjusted to 2.8, 5.6, 8.4, 11.2, 14.0, and 16.8 weight % by varying a concentration of a vanadium oxalic acid aqueous solution, thereby producing six species of magnesia-zirconia complex carrier-supported magnesium orthovanadate catalysts. Each catalyst was referred to as X-VMgO/MgO—ZrO$_2$ (X=vanadium content) depending on the vanadium content.

Preparation Example 5

Production of Five Species of Magnesium Orthovanadate Catalysts Containing Vanadium Supported by Magnesia-Zirconia Complex Carrier (MgO—ZrO$_2$) at Various Ratios Prepared by Sol-Gel Method Magnesia-zirconia complex carriers containing magnesia and zirconia at various ratios were prepared by the methods of Preparation Examples 1 and 2 of the present invention, and five species of magnesium orthovanadate catalysts containing vanadium of 11.2 weight % were prepared. To be specific, when magnesia-zirconia was prepared by a sol-gel method, a carrier was prepared such that ratios of magnesia and zirconia in the magnesia-zirconia complex carrier were 16:1, 8:1, 4:1, 2:1 and 1:1, and an amount of vanadium to be supported was adjusted to 11.2 weight %, thereby producing five species of magnesia-zirconia complex carrier-supported magnesium orthovanadate catalysts.

Example 1

Oxidative Dehydrogenation of n-Butane by Using Continuous Flow Type Catalyst Reactor The oxidative dehydrogenation of n-butane was carried out by using the magnesia-zirconia complex carrier-supported magnesium orthovanadate catalyst prepared by the method according to the preparation examples 1 and 2 under the conditions as described below.

The reactant for the oxidative dehydrogenation of n-butane in this example 1 was a C4 mixture containing 99.4 wt % of n-butane, and the specific composition thereof was represented in the following table 1.

TABLE 1

| Composition of C4 mixture used as a reactant | | |
|---|---|---|
| Composition | Molecular formula | Wt % |
| i-butane | $C_4H_{10}$ | 0.18 |
| n-butane | $C_4H_{10}$ | 99.40 |
| 1-butene | $C_4H_8$ | 0.34 |
| cis-2-butene | $C_4H_8$ | 0.08 |
| Total | | 100.00 |

The C4 mixture as a reactant was fed in the form of a mixed gas with oxygen and nitrogen.

The composition ratio of the reactant was determined based on the amount of n-butane in the C4 mixture, to be n-butane:oxygen:nitrogen of 4:8:88 by volume.

The reaction was carried out by fixing the catalyst powder in a linear quartz reactor for the catalyst reaction, maintaining the reaction temperature of the catalyst bed by placing the reactor in an electric furnace, and letting the reactant continuously passed the catalyst bed inside the reactor thereby proceeding with the reaction.

The amount of catalyst was set to achieve the feeding speed of the reactant to be 2000 h$^{-1}$ based on n-butane. Before flowing the reactant, the temperature of the reactor with the fixed bed was elevated from a room temperature to 500° C. for catalyst activation, while flowing nitrogen and oxygen, and the reaction temperature, i.e. the temperature of the catalyst bed of the fixed bed reactor was maintained at 500° C., while flowing n-butane as reactant. Since the product obtained from the reaction contained carbon dioxide from complete oxidation, side products from cracking, other side products for example from an isomerization reaction and unreacted n-butane, other than the main products n-butene and 1,3-butadiene, gas chromatography was used to separate and analyze them. The n-butane conversion rate, the selectivity to dehydrogenation products and yield of the oxidative dehydrogenation of n-butane carried out on the magnesia-zirconia complex carrier-supported magnesium orthovanadate catalyst were calculated by the following equation 1, 2 and 3.

$$\text{conversion rate}(\%) = \frac{\text{mole number of reacted n-butane}}{\text{mole number of fed n-butane}} \times 100 \quad [\text{Equation 1}]$$

$$\text{selectivity}(\%) = \frac{\text{mole number of the resulted dehydrogenation product}}{\text{mole number of the reacted n-butane}} \times 100 \quad [\text{Equation 2}]$$

$$\text{Yield }(\%) = \frac{\text{mole number of the resulted dehydration product}}{\text{mole number of n-butane fed}} \times 100 \quad [\text{Equation 3}]$$

The oxidative dehydrogenation of n-butane was carried out on each of the magnesia-zirconia complex carrier-supported magnesium orthovanadate catalysts prepared by the sol-gel method according to the preparation examples 1 and 2 for 12 hours. The catalytic reaction activities over time during 12 hours were represented in the FIG. 1, and the results after 12 hours of the reaction were represented in the following Table 2 and FIG. 2.

TABLE 2

Catalytic activity of magnesium orthovanadate catalyst (VMgO/MgO—ZrO$_2$) containing vanadium of 5.6 weight % supported by magnesia-zirconia complex carrier prepared by sol-gel method for 12 hours after oxidative dehydrogenation reaction

| Catalyst | Normal-butane conversion rate (%) | Dehydrogenation product selectivity (%) | Dehydrogenation product yield (%) |
|---|---|---|---|
| 5.6-VMgO/MgO—ZrO$_2$ (Sol-gel method) | 49.5 | 42.3 | 20.9 |

Comparative Example 1

Figure 1:
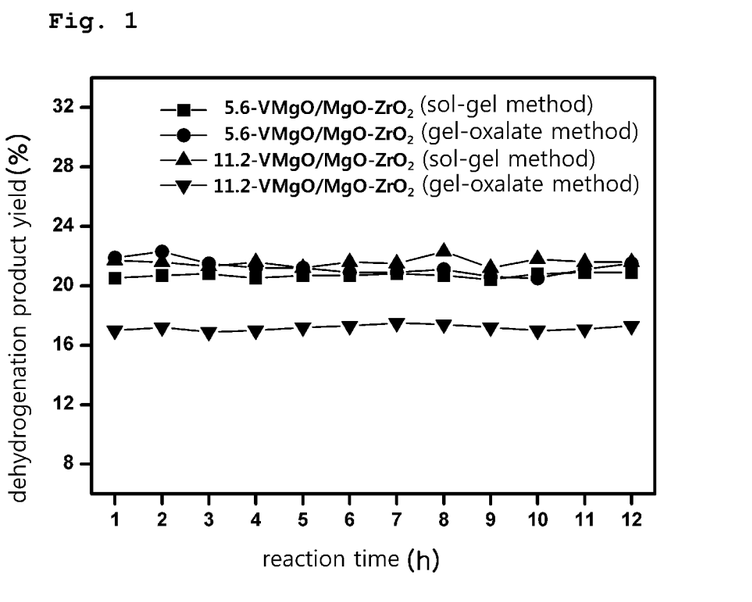
FIG. 1 is a plot representing the catalyst activity changes over time and differences thereof in oxidative dehydrogenation of n-butane using the magnesia-zirconia complex carrier-supported magnesium orthovanadate catalyst according to the example 1 of the present invention and the comparative examples 1 and 2.
Figure 2:
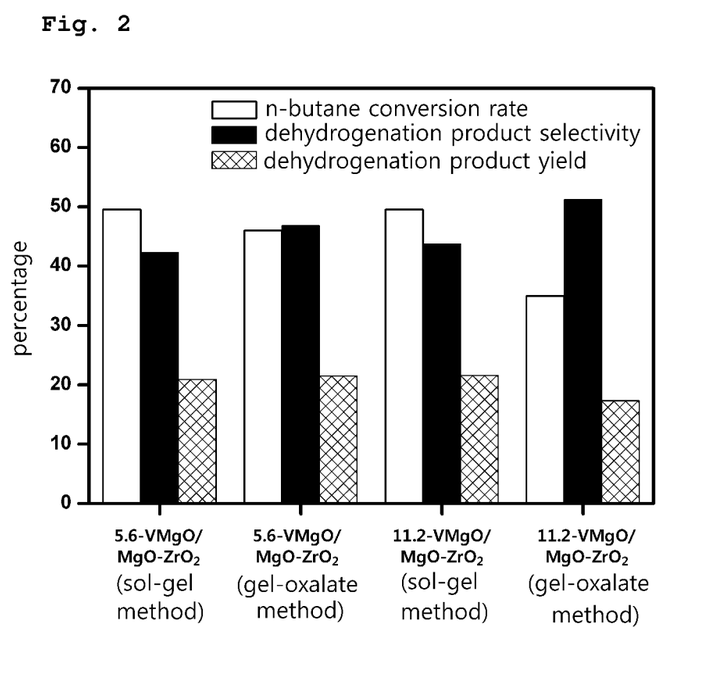
FIG. 2 is a plot representing the catalyst activity differences in oxidative dehydrogenation of n-butane, after 12 hours of the oxidative dehydrogenation using the magnesia-zirconia complex carrier-supported magnesium orthovanadate catalyst according to the example 1 of the present invention and the comparative examples 1 and 2.

Oxidative Dehydrogenation Activity of Magnesium Orthovanadate Catalyst (VMgO/MgO—ZrO$_2$) Containing Vanadium of 5.6 Weight % Supported by Magnesia-Zirconia Complex Carrier Prepared by Gel-Oxalate Method For comparison with the result of oxidative dehydrogenation activity with a magnesia-zirconia complex carrier-supported magnesium orthovanadate catalyst prepared by the sol-gel method, according to Example 1 of the present invention, an oxidative dehydrogenation reaction of n-butane was carried out in the order as described in Example 1 using the magnesium orthovanadate catalyst supported by the magnesia-zirconia complex carrier, which was prepared by the gel-oxalate method reported in the previous patent of the present inventors, according to Comparative Preparation Example 1 and Preparation Example 2. The result of the reaction experiment according to this Comparative Example 1 was as listed in Table 3 and illustrated in FIGS. 1 and 2. FIG. 1 illustrates the progress of reaction activity for 12 hours, and Table 3 lists and FIG. 2 illustrates the result after an oxidative dehydrogenation reaction of n-butane with a magnesia-zirconia complex carrier-supported magnesium orthovanadate catalyst prepared by a gel-oxalate method was carried out for 12 hours in the same manner as Example 1.

TABLE 3

Catalytic activity of magnesium orthovanadate catalyst containing vanadium of 5.6 weight % supported by magnesia-zirconia complex carrier (VMgO/MgO—ZrO$_2$) prepared by gel-oxalate method after 12 hours of oxidative dehydrogenation reaction

| Catalyst | Normal-butane conversion rate (%) | Dehydrogenation product selectivity (%) | Dehydrogenation product yield (%) |
|---|---|---|---|
| 5.6-VMgO/MgO—ZrO$_2$ (Gel-oxalate method) | 46 | 46.8 | 21.5 |

Example 2 and Comparative Example 2

Oxidative Dehydrogenation Activity of Magnesium Orthovanadate Catalysts Containing Vanadium of 11.2 Weight % Supported by Magnesia-Zirconia Complex Carrier (VMgO/MgO—ZrO$_2$) Prepared by Gel-Oxalate Method and Sol-Gel Method For comparison with the results of oxidative dehydrogenation activity with magnesia-zirconia complex carrier-supported magnesium orthovanadate catalysts respectively prepared by the sol-gel method and the gel-oxalate method, according to Example of the present invention and Comparative Example 1, an oxidative dehydrogenation reaction of n-butane was carried out in the order as described in Example 1 using each of the magnesium orthovanadate catalyst supported by the magnesia-zirconia complex carriers prepared by the methods of Preparation Examples 1 and 3 (Example 2) and the magnesium orthovanadate catalyst supported by the magnesia-zirconia complex carriers prepared by the methods of Comparative Preparation Example 1 and Preparation Example 3 (Comparative Example 2). Results of the reaction experiments according to Example 2 and Comparative Example 2 were as listed in Table 4 and illustrated in FIGS. 1 and 2. FIG. 1 illustrates the progress of catalytic activity during the oxidative dehydrogenation reaction for 12 hours, and Table 4 lists and FIG. 2 illustrates reaction results after oxidative dehydrogenation reactions of n-butane with magnesia-zirconia complex carrier-supported magnesium orthovanadate catalysts were carried out for 12 hours.

TABLE 4

Catalytic activity of magnesium orthovanadate catalysts containing vanadium of 11.2 weight % supported by magnesia-zirconia complex carrier (VMgO/MgO—ZrO$_2$) prepared by sol-gel method and gel-oxalate method after 12 hours of oxidative dehydrogenation reaction

| Catalyst | Normal-butane conversion rate (%) | Dehydrogenation product selectivity (%) | Dehydrogenation product yield (%) |
|---|---|---|---|
| 11.2-VMgO/MgO—ZrO$_2$ (Sol-gel method) | 49.5 | 43.7 | 21.6 |
| 11.2-VMgO/MgO—ZrO$_2$ (Gel-oxalate method) | 35 | 51.2 | 17.3 |

When the magnesia-zirconia complex carrier-supported magnesium orthovanadate catalysts prepared by the sol-gel method and the gel-oxalate method were used in an oxidative dehydrogenation reaction, the results of the reaction experiments according to Examples 1 and 2 and Comparative Examples 1 and 2 were compared in order to observe differences in effect of each complex carrier in the magnesium orthovanadate catalysts. The results of reaction experiments after an oxidative dehydrogenation reaction of n-butane for 12 hours were put together as listed in Table 5 and illustrated in FIGS. 1 and 2.

TABLE 5

Comparison among magnesia-zirconia complex carrier-supported magnesium orthovanadate catalysts in activity after 12 hours oxidative dehydrogenation reaction

| Catalyst | Normal-butane conversion rate (%) | Dehydrogenation product selectivity (%) | Dehydrogenation product yield (%) |
|---|---|---|---|
| 5.6-VMgO/MgO—ZrO$_2$ (Sol-gel method) | 49.5 | 42.3 | 20.9 |
| 5.6-VMgO/MgO—ZrO$_2$ (Gel-oxalate method) | 46 | 46.8 | 21.5 |
| 11.2-VMgO/MgO—ZrO$_2$ (Sol-gel method) | 49.5 | 43.7 | 21.6 |
| 11.2-VMgO/MgO—ZrO$_2$ (Gel-oxalate method) | 35 | 51.2 | 17.3 |

According to Table 5 and FIGS. 1 and 2, it can be seen that the magnesia-zirconia complex carrier-supported magnesium orthovanadate catalysts prepared by the sol-gel method were approximately equal to or higher than the magnesia-zirconia complex carrier-supported magnesium orthovanadate catalysts prepared by the gel-oxalate method in catalytic activity. It can be seen that the change of the yield according to the change of the vanadium content is not large, and generally, a high yield can be obtained. Therefore, it was confirmed that the magnesia-zirconia complex carrier prepared by the sol-gel method according to the present invention is suitable for a carrier for an oxidative dehydrogenation reaction of n-butane, and, thus, a production method of a magnesium orthovanadate catalyst containing vanadium supported by magnesia-zirconia complex carrier prepared by the sol-gel method using a citric acid according to the present invention could be established.

FIG. 1 illustrates the progress of activities of magnesia-zirconia complex carrier-supported magnesium orthovanadate catalysts over time in an oxidative dehydrogenation reaction of n-butane. Any change such as deactivation of the complex carrier-based catalysts prepared by the sol-gel method or the gel-oxalate method was not observed, and, thus, it was confirmed that all of these four catalysts are thermally and chemically stable in an oxidative dehydrogenation reaction of n-butane.

Example 3

Oxidative Dehydrogenation Activities of Magnesia-Zirconia Complex Carrier-Supported Magnesium Orthovanadate Catalysts with Various Contents of Vanadium (X-VMgO/MgO—$ZrO_2$, X=V Content) Prepared by Sol-Gel Method An oxidative dehydrogenation reaction of n-butane was carried out in the order as described in Example 1 using each of magnesium orthovanadate catalysts with various contents of vanadium supported by magnesia-zirconia complex carrier, which were prepared by sol-gel method, according to Preparation Example 4 of the present invention. Table 6 and FIG. 3 provide the results of the reaction experiment according to this Example 3 exhibiting a change in activity of each catalyst over time in an oxidative dehydrogenation reaction of n-butane.

Figure 3:
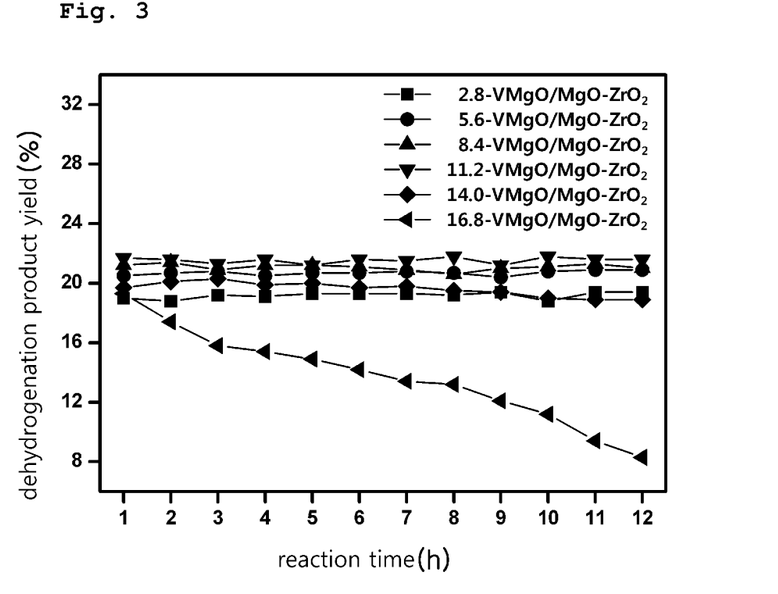
FIG. 3 is a plot representing the catalyst activity changes over time and differences thereof in oxidative dehydrogenation of n-butane using each of 6 species of the magnesia-zirconia complex carrier-supported magnesium orthovanadate catalysts containing various amount of vanadium according to the example 1 of the present invention and the comparative example 3.

According to Table 6 and FIG. 3, it can be seen that the catalytic activity of the magnesia-zirconia complex carrier-supported magnesium orthovanadate catalyst varied depending on the vanadium content. In particular, in the case of vanadium of 16.8 weight %, the reaction activity of the catalyst was suddenly deactivated at a certain point in time unlike the other catalysts and lost its catalytic activity. However, as for the magnesium orthovanadate catalysts with other vanadium contents than the vanadium content of 16.8 weight %, an oxidative dehydrogenation reaction of n-butane was stably carried out for 12 hours. Further, it was observed that all of these catalysts were not greatly changed in catalytic activity in spite of a change in vanadium content and had a relatively high activity.

According to the above results, in order to expect a synergy effect of catalytic activity between magnesium orthovanadate and a magnesia-zirconia carrier, vanadium in an amount of preferably 2.8 weight % to 14.0 weight %, more preferably 11.2 weight % may be supported by a complex carrier having a molar ratio of magnesia:zirconia of 4:1.

Example 4

Figure 4:
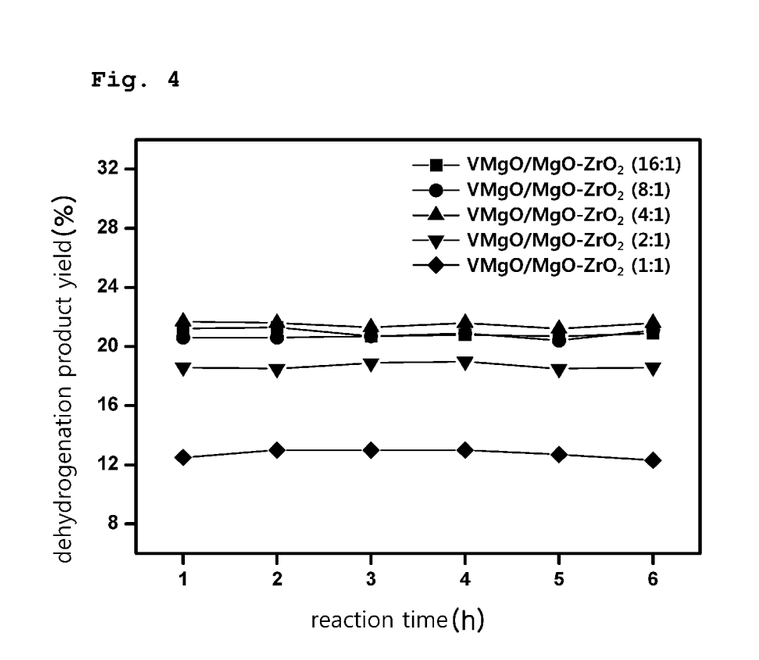
FIG. 4 is a plot representing the catalyst activity changes over time and differences thereof in oxidative dehydrogenation of n-butane using each of 5 species of the magnesia-zirconia complex carrier-supported magnesium orthovanadate catalysts having various molar ratios of magnesia and zirconia according to the example 1 of the present invention and the comparative example 4.

Oxidative Dehydrogenation Activity of Magnesia-Zirconia Complex Carrier-Supported Magnesium Orthovanadate Catalysts Containing Vanadium of 11.2 Weight % (11.2-VMgO/MgO—$ZrO_2$) Prepared by Sol-Gel Method at Various Ratios of Magnesia and Zirconia In order to check an optimum ratio of magnesia and zirconia in a magnesia-zirconia complex carrier-supported magnesium orthovanadate catalyst prepared by a sol-gel method, an oxidative dehydrogenation reaction of n-butane was carried out in the order as described in Example 1 using each of magnesium orthovanadate catalysts containing vanadium of 11.2 weight % supported by a magnesia-zirconia complex carrier, which were prepared by a sol-gel method at various ratios of magnesia and zirconia, according to Preparation Example 5 of the present invention. Table 7 and FIG. 4 provide the results of the reaction experiment according to this Example 4 exhibiting a change in activity of each catalyst over time in an oxidative dehydrogenation reaction of n-butane.

TABLE 6

Progress of oxidative dehydrogenation activity of magnesia-zirconia complex carrier-based magnesium orthovanadate catalysts with various contents of vanadium prepared by sol-gel method over time

| | Dehydrogenation product yield (%) Time (h) | | | | | | | | | | | |
|---|---|---|---|---|---|---|---|---|---|---|---|---|
| Catalyst | 1 | 2 | 3 | 4 | 5 | 6 | 7 | 8 | 9 | 10 | 11 | 12 |
| 2.8-VMgO/MgO—$ZrO_2$ | 19.0 | 18.8 | 19.2 | 19.1 | 19.3 | 19.3 | 19.3 | 19.2 | 19.4 | 18.8 | 19.4 | 19.4 |
| 5.6-VMgO/MgO—$ZrO_2$ | 20.5 | 20.7 | 20.8 | 20.5 | 20.7 | 20.7 | 20.8 | 20.7 | 20.4 | 20.8 | 20.9 | 20.9 |
| 8.4-VMgO/MgO—$ZrO_2$ | 21.2 | 21.4 | 20.9 | 21.2 | 21.2 | 21.1 | 20.9 | 20.6 | 21.0 | 21.1 | 21.3 | 21.0 |
| 11.2-VMgO/MgO—$ZrO_2$ | 21.7 | 21.6 | 21.3 | 21.6 | 21.2 | 21.6 | 21.5 | 21.8 | 21.2 | 21.8 | 21.6 | 21.6 |
| 14.0-VMgO/MgO—$ZrO_2$ | 19.7 | 20.1 | 20.3 | 19.9 | 20.0 | 19.7 | 19.8 | 19.5 | 19.4 | 19.0 | 18.9 | 18.9 |
| 16.8-VMgO/MgO—$ZrO_2$ | 19.3 | 17.4 | 15.8 | 15.4 | 14.9 | 14.2 | 13.4 | 13.2 | 12.1 | 11.2 | 9.4 | 8.3 |

TABLE 7

Progress of oxidative dehydrogenation activity of magnesia-zirconia complex carrier-supported magnesium orthovanadate catalysts containing vanadium of 11.2 weight % prepared by sol-gel method at various ratios of magnesia and zirconia over time

| Catalyst | Dehydrogenation product yield (%) Time (h) | | | | | |
|---|---|---|---|---|---|---|
| | 1 | 2 | 3 | 4 | 5 | 6 |
| VMgO/MgO—ZrO$_2$(16:1) | 21.2 | 21.3 | 20.7 | 20.8 | 20.7 | 20.9 |
| VMgO/MgO—ZrO$_2$(8:1) | 20.6 | 20.6 | 20.7 | 20.9 | 20.4 | 21.1 |
| VMgO/MgO—ZrO$_2$(4:1) | 21.7 | 21.6 | 21.3 | 21.6 | 21.2 | 21.6 |
| VMgO/MgO—ZrO$_2$(2:1) | 18.6 | 18.5 | 18.9 | 19.0 | 18.5 | 18.6 |
| VMgO/MgO—ZrO$_2$(1:1) | 12.5 | 13.0 | 13.0 | 13.0 | 12.7 | 12.3 |

According to Table 7 and FIG. 4, it can be seen that in the oxidative dehydrogenation reaction of n-butane using the magnesia-zirconia complex carrier-supported magnesium orthovanadate catalysts prepared by varying a ratio of magnesia:zirconia, as a ratio of magnesia:zirconia in the catalyst was changed, activity was also changed, and overall, a high activity was obtained from all of the catalysts. According to the above results, it can be seen that the magnesia-zirconia complex carrier-supported magnesium orthovanadate catalysts containing vanadium prepared by the sol-gel method using a citric acid generally exhibited a high activity and the activity thereof varied depending on variations in amounts of vanadium, magnesia and zirconia. In particular, the catalyst 11.2-VMgO/MgO—ZrO$_2$ (4:1) having a vanadium content of 11.2 weight % and a molar ratio of magnesia:zirconia of 4:1 exhibited the highest reaction activity. Therefore, it can be seen that a catalyst capable of obtaining the most dehydrogenation product from an oxidative dehydrogenation reaction of n-butane was the catalyst 11.2-VMgO/MgO—ZrO$_2$ (4:1) having a molar ratio of magnesia:zirconia of 4:1 and a vanadium content of 11.2 weight %.

REFERENCES

Patented Document

1. U.S. Pat. No. 6,433,241 (A. Wu, C. A. Frake) Aug. 13, 2002.
2. U.S. Pat. No. 6,187,984 (A. Wu, C. A. Frake) Feb. 13, 2001.
3. Korean Patent Application No. 10-2011-0021037
4. Korean Patent Application No. 10-2011-00512935
5. Korean Patent Application No. 10-2011-0101954
6. U.S. Pat. No. 3,914,332 (A. F. Dickason) Oct. 21, 1975.
7. U.S. Pat. No. 3,303,234 (L. Bajars, L. J. Croce) Feb. 7, 1967.

Non-Patented Document

1. N. Kijima, M. Toba, Y. Yoshimura, Catal. Lett., vol. 127, p. 3 (2009).
2. I. C. Marcu, I. Sandulescu, J. M. M. Millet, Appl. Catal. A, vol. 227, p. 309 (2002).
3. L. M. Madeira, J. M. Herrmann, F. G. Freire, M. F. Portela, F. J. Maldonado, Appl. Catal. A, vol. 158, p. 243 (1997).
4. A. A. Lemonidou, G. J. Tjatjopoulos, I. A. Vasalos, Catal. Today, vol. 45, p. 65 (1998).
5. H. H. Kung, Ind. Eng. Chem. Prod. Res. Dev., vol. 25, p. 171 (1986).
6. M. A. Chaar, D. Partel, H. H. Kung, J. Catal., vol. 105, p. 483 (1987).
7. M. A. Chaar, D. Partel, H. H. Kung, J. Catal., vol. 109, p, 463 (1988).
8. O. S. Owen, H. H. Kung, J. Mol. Catal., vol. 79, p. 265 (1993).
9. M. E. Harlin, V. M. Niemi, A. O. I. Krause, J. Catal. vol. 195, p. 67 (2000).
10. V. M. Murgia, E. M. F. Torres, J. C. Gottifredi, E. L. Sham, Appl. Catal. A, vol. 312, p. 134 (2006).
11. F. Urlan, I. C. Marcu, I. Sandulescu, Catal. Commun., vol. 9, p. 2403 (2008).
12. H. Armendariz, J. A. Toledo, G. Aguilar-Rios, M. A. Valenzuela, P. Salas, A. Cabral, H. Jimenez, I. Schifter, J. Mol. Catal., vol. 92, p. 325 (1994).
13. H. H. Kung, Ind. Eng. Chem. Prod. Res. Dev., vol. 25, p. 171 (1986).
14. J. M. Lopez Nieto, A. Dejoz, M. J. Vazquez, W. O'Leary, J. Cunnungham, Catal. Today, vol. 40, p. 215 (1998).
15. D. Bhattacharyya, S. K. Bej, M. S. Rao, Appl. Catal. A, vol. 87, p. 29 (1992).

What is claimed is:

1. A method for preparing n-butene and 1,3-butadiene, comprising:
   (a) preparing a mixed precursor solution of magnesium and zirconium by dissolving a magnesium precursor and a zirconium precursor in a first solvent;
   (b) preparing a solid acid solution by dissolving at least one solid acid selected from the group consisting of citric acid, succinic acid, malic acid, and tartaric acid in a second solvent;
   (c) preparing a carrier forming solution by mixing the mixed precursor solution prepared in the step (a) and the solid acid solution prepared in the step (b);
   (d) producing a magnesia-zirconia complex carrier by heat-drying the carrier forming solution prepared in the step (c) and heating a resultant solid product;
   (e) impregnating the magnesia-zirconia complex carrier prepared in the step (d) with an aqueous vanadate solution;
   (f) preparing a magnesia-zirconia complex carrier-supported magnesium orthovanadate catalyst by heating the product obtained from the step (e); and
   (g) carrying out an oxidative dehydrogenation of n-butane on the magnesia-zirconia complex carrier-supported magnesium orthovanadate catalyst prepared in the step (f) with a mixed gas comprising n-butane, oxygen and nitrogen as a reactant.

2. The method according to claim 1, wherein the oxidative dehydrogenation of n-butane in the step (g) carried out at the temperature of 300-800° C.

3. The method according to claim 1, wherein the mixed gas used in the step (g) comprises n-butane, oxygen and nitrogen, at the ratio by volume of n-butane:oxygen:nitrogen=2-10:0.5-40:50-97.5.

4. The method according to claim 1, wherein the magnesium precursor used in the step (a) includes at least one selected from a chloride or a nitrate of magnesium, and the zirconium precursor used in the step (a) includes at least one selected from a chloride, an oxynitrate, or oxychloride of zirconium.

5. The method according to claim 1, wherein the first solvent used in the step (a) and the second solvent used in the step (b) are independently selected from water and alcohol.

6. The method according to claim 1, wherein the drying in the step (d) is carried out at 40-200° C., and heating is carried out at 400-1000° C.

7. The method according to claim 1, wherein the heating in the step (f) is carried out at 350-800° C. for 1-6 hours.

* * * * *